(12) United States Patent
Wiener et al.

(10) Patent No.: US 7,476,233 B1
(45) Date of Patent: Jan. 13, 2009

(54) ULTRASONIC SURGICAL SYSTEM WITHIN DIGITAL CONTROL

(75) Inventors: Eitan T. Wiener, Cincinnati, OH (US); William T. Donofrio, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1224 days.

(21) Appl. No.: 09/693,621

(22) Filed: Oct. 20, 2000

(51) Int. Cl.
  *H03L 7/10* (2006.01)
(52) U.S. Cl. .................................... 606/169
(58) Field of Classification Search ................ 606/166, 606/169, 170, 171, 176, 177, 178, 179, 127, 606/167, 180, 32, 39, 41, 42
See application file for complete search history.

(56) References Cited

U.S. PATENT DOCUMENTS

| | | | |
|---|---|---|---|
| 2,917,691 A | 12/1959 | DePrisco et al. ............ 318/118 |
| 4,879,528 A | 11/1989 | Gotanda | |
| 4,965,532 A | 10/1990 | Sakurai | |
| 5,001,649 A | 3/1991 | Lo et al. ...................... 364/484 |
| 5,026,387 A | 6/1991 | Thomas ...................... 606/169 |
| 5,112,300 A | 5/1992 | Ureche ........................ 604/22 |
| 5,180,363 A | 1/1993 | Idemoto et al. ............... 202/32 |
| 5,400,267 A | 3/1995 | Denen et al. ................. 364/552 |
| 5,425,704 A | 6/1995 | Sakurai et al. ................ 604/22 |
| 5,449,370 A | 9/1995 | Vaitekunas .................. 606/169 |
| 5,451,161 A | 9/1995 | Sharp | |
| 5,630,420 A | 5/1997 | Vaitekunas ............. 128/662.03 |
| 5,652,479 A | 7/1997 | LoCascio et al. | |
| 5,707,369 A | 1/1998 | Vaitekunas et al. ............ 606/31 |
| 5,879,364 A | 3/1999 | Bromfield et al. ............ 606/169 |
| 5,897,569 A * | 4/1999 | Kellogg et al. ............... 606/169 |
| 5,931,836 A * | 8/1999 | Hatta et al. ..................... 606/38 |
| 5,968,007 A | 10/1999 | Simon et al. ................... 604/22 |
| 6,017,354 A | 1/2000 | Culp et al. .................. 606/170 |
| 6,019,775 A | 2/2000 | Sakurai ....................... 606/169 |
| 6,066,135 A | 5/2000 | Honda | |
| 6,090,123 A | 7/2000 | Culp et al. .................. 606/180 |
| 6,511,478 B1 * | 1/2003 | Burnside et al. ............... 606/41 |

FOREIGN PATENT DOCUMENTS

| | | |
|---|---|---|
| EP | 0 875 301 A2 | 11/1998 |
| EP | 1 025 806 A1 | 8/2000 |
| JP | 2000-175926 | 6/2000 |
| WO | WO 00/51508 | 9/2000 |

OTHER PUBLICATIONS

European Search Report dated Jan. 9, 2004.

* cited by examiner

*Primary Examiner*—Steven O Douglas
(74) *Attorney, Agent, or Firm*—Verne E. Kreger, Jr.

(57) ABSTRACT

An ultrasonic surgical system utilizes a digital control system to generate ultrasonic drive current for transducers that are located in a hand piece and are attached to a surgical scalpel or blade so as to vibrate the blade in response to the current. The digital control includes a digital signal processor (DSP) or microprocessor; a direct digital synthesis (DDS) device; a phase detection logic scheme, a control algorithm for seeking and maintaining resonance frequency; and design scheme that allows to regulate current, voltage, and power delivered to an ultrasonic device. The system allows the power versus load output curve to be tailored to a specific hand piece; the components of the digital system are much less sensitive to temperature variations; and the digital system provides increased flexibility in locating the resonance frequency of the blade and running diagnostic tests.

14 Claims, 6 Drawing Sheets

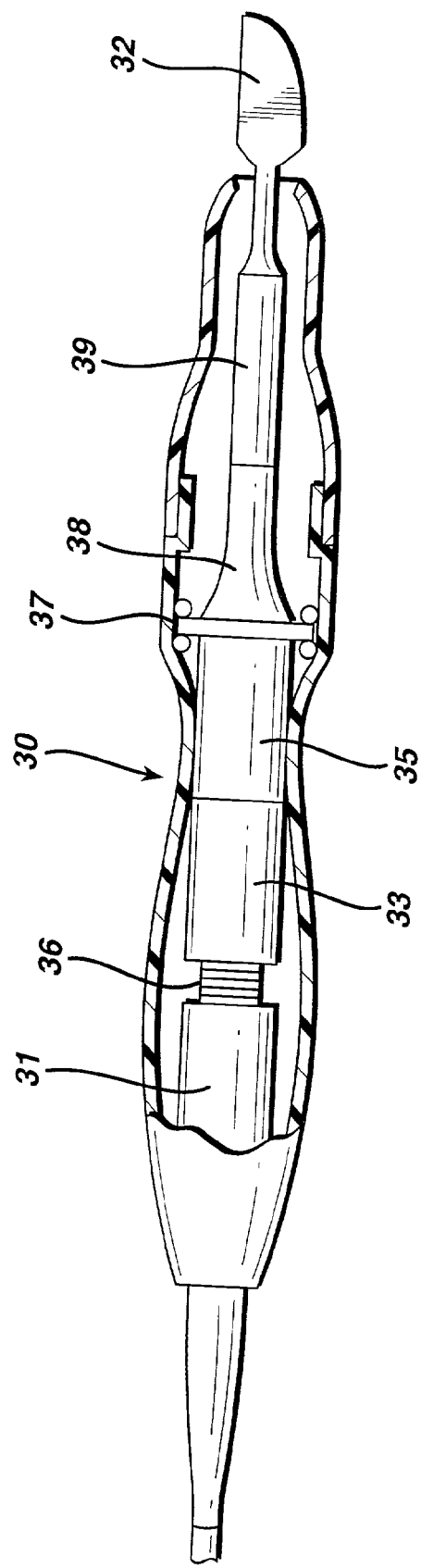

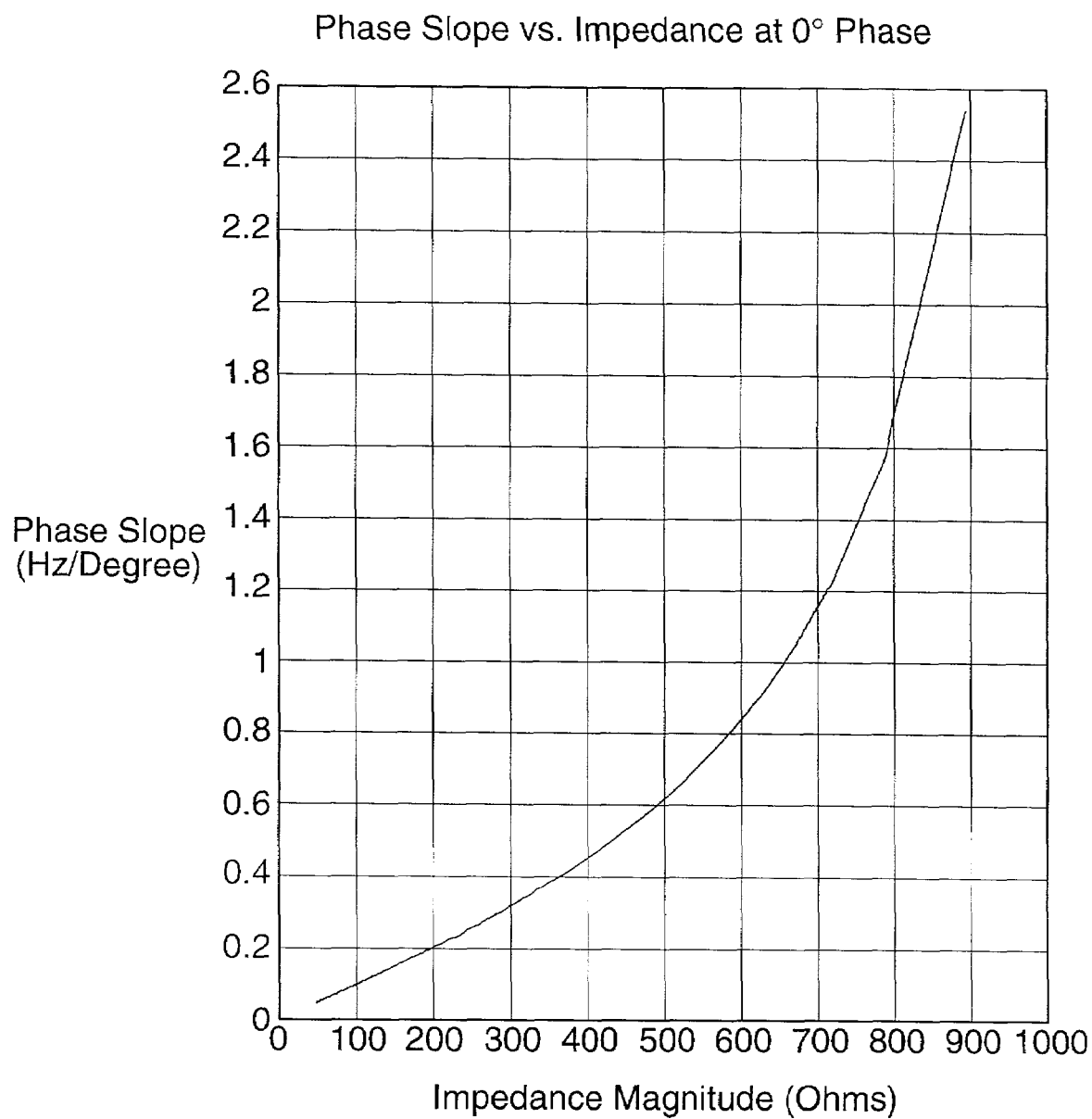

ULTRASONIC SURGICAL SYSTEM WITHIN DIGITAL CONTROL

BACKGROUND OF THE INVENTION

1. Field of the Invention

This invention relates to ultrasonic surgical systems and, more particularly, to improved apparatus for facilitating the performance of surgical procedures such as simultaneous soft tissue dissection and cauterization of large and small blood vessels through the use of a precisely controlled ultrasonically vibrating blade or scalpel.

2. Description of the Related Art

It is known that electric scalpels and lasers can be used as surgical instruments to perform the dual function of simultaneously effecting the incision and hemostatis of soft tissue by cauterizing tissue and blood vessels. However, such instruments employ very high temperatures to achieve coagulation, causing vaporization and fumes as well as splattering, which increases the risk of spreading infectious diseases to operating room personnel. Additionally, the use of such instruments often results in relatively wide zones of thermal tissue damage.

Cutting and cauterizing of tissue by means of surgical blades vibrated at high speeds by ultrasonic drive mechanisms is also well known. One of the problems associated with such ultrasonic cutting instruments is uncontrolled or undamped vibrations, and the heat as well as material fatigue resulting therefrom. In an operating room environment, attempts have been made to control this heating problem by the inclusion of cooling systems with heat exchangers to cool the blade. In one known system, for example, the ultrasonic cutting and tissue fragmentation system requires a cooling system augmented with a water circulating jacket and means for irrigation and aspiration of the cutting site. Another known system requires the delivery of cryogenic fluids to the cutting blade.

It is known to limit the current delivered to the transducer as a means for limiting the heat generated therein. However, this could result in insufficient power to the blade at a time when it is needed for the most effective treatment of the patient. U.S. Pat. No. 5,026,387 to Thomas, which is assigned to the assignee of the present application, discloses a system for controlling the heat in an ultrasonic surgical cutting and hemostasis system without the use of a coolant, by controlling the drive energy supplied to the blade. In the system according to this patent, an ultrasonic generator is provided which produces an electrical signal of a particular voltage, current and frequency, e.g., 55,500 cycles per second. The generator is connected by a cable to a hand piece, which contains piezoceramic elements forming an ultrasonic transducer. In response to a switch on the hand piece or a foot switch connected to the generator by another cable, the generator signal is applied to the transducer, which causes a longitudinal vibration of its elements. A structure connects the transducer to a surgical blade, which is thus vibrated at ultrasonic frequencies when the generator signal is applied to the transducer. The structure is designed to resonate at the selected frequency, thus amplifying the motion initiated by the transducer.

The signal provided to the transducer is controlled so as to provide power on demand to the transducer in response to the continuous or periodic sensing of the loading condition (tissue contact or withdrawal) of the blade. As a result, the device goes from a low power (idle) state to a selectable high power (cutting) state automatically depending on whether the scalpel is or is not in contact with tissue. A third, high power coagulation mode is manually selectable with automatic return to an idle power level when the blade is not in contact with tissue. Since the ultrasonic power is not continuously supplied to the blade, it generates less ambient heat, but imparts sufficient energy to the tissue for incisions and cauterization when necessary.

The control system in the Thomas patent is of the analog type. A phase lock loop that includes a voltage controlled oscillator, a frequency divider, a power switch, a matching network and a phase detector, stabilizes the frequency applied to the hand piece. A microprocessor controls the amount of power by sampling the frequency current and voltage applied to the hand piece, because these parameters change with load on the blade.

The power versus load curve in a generator in a typical ultrasonic surgical system, such as that described in the Thomas patent, has two segments. The first segment has a positive slope of increasing power, as the load is increased, which indicates constant current delivery. The second segment has a negative slope of decreasing power as the load increases, which indicates a constant or saturated output voltage. The regulated current for the first segment is fixed by the design of the electronic components, and the second segment voltage is limited by the maximum output voltage of the design. This arrangement is inflexible since the power versus load characteristics of the output of such a system can not be optimized to various types of hand piece transducers and ultrasonic blades. The performance of traditional analog ultrasonic power systems for surgical instruments is affected by the component tolerances and their variability in the generator electronics due to changes in operating temperature. In particular, temperature changes can cause wide variations in key system parameters, such as frequency lock range, drive signal level, and other system performance measures.

In order to operate an ultrasonic surgical system in an efficient manner, during startup the frequency of the signal supplied to the hand piece transducer is swept over a range to locate the resonance frequency. Once it is found, the generator phase locks on to the resonance frequency, keeps monitoring of the transducer current to voltage phase angle and maintains the transducer resonating by driving it at the resonance frequency. A key function of such a system is to maintain the transducer resonating across load and temperature changes that vary the resonance frequency. However, these traditional ultrasonic drive systems have little to no flexibility with regards to adaptive frequency control. Such flexibility is key to the system's ability to discriminate undesired resonances. In particular, these systems can only search for resonance in one direction, i.e., with increasing or decreasing frequencies, and their search pattern is fixed. The system cannot hop over other resonance modes or make any heuristic decisions, such as what resonance(s) to skip or lock onto, and ensure delivery of power only when appropriate frequency lock is achieved.

The prior art ultrasonic generator systems also have little flexibility with regard to amplitude control, which would allow the system to employ adaptive control algorithms and decision making. For example, these fixed systems lack the ability to make heuristic decisions with regards to the output drive, e.g., current or frequency, based on the load on the blade and/or the current-to-voltage phase angle. It also limits the system's ability to set optimal transducer drive signal levels for consistent efficient performance, which would increase the useful life of the transducer and ensure safe operating conditions for the blade. Further, the lack of control over amplitude and frequency control reduces the system's ability to perform diagnostic tests on the transducer/blade system and to support troubleshooting in general.

Some limited diagnostic tests performed in the past involve sending a signal to the transducer to cause the blade to move and the system to be brought into resonance or some other vibration mode. Then the response of the blade is determined by measuring the electrical signal supplied to the transducer when the system is in one of these modes. The new system has the ability to sweep the output drive frequency, monitor the frequency response of the ultrasonic transducer and blade, extract parameters from this response, and use these parameters for system diagnostics. This frequency sweep and response measurement mode is achieved via a digital code such that the output drive frequency can be stepped with high resolution, accuracy, and repeatability not existent in prior art. As a result, extensive and accurate diagnostics can be performed.

A particular operation may make use of an ultrasonic surgical instrument followed or preceded by the use of an Electro-surgical Unit ("ESU") in which a high frequency electric current is delivered through the tissue under treatment and acts as a combination scalpel and cauterizing instrument. However, an ESU can emit a large amount of electrical interference when activated. This interference can impair the reliable operation of the ultrasonic surgical equipment, which may be activated at the same time. Thus, there is a need for a means to temporarily disable the ultrasonic surgical equipment during ESU activation. In the prior art this has been accomplished by hardwiring the ultrasonic equipment and the ESU together such that when the ESU is activated, the ultrasonic equipment is disabled. However, this can be inconvenient, since both instruments must be brought into the operating area, even if only one is going to be used.

SUMMARY OF THE INVENTION

The present invention is directed to eliminating problems in an ultrasonic surgical system that includes an ultrasonic generator that drives a hand piece with an ultrasonic blade or scalpel. These problems include difficulty in locating the mechanical resonance of the blade, excessive heat in the blade, temperature dependence of the components of the ultrasonic generator, inconsistent blade performance, reduced diagnostic capability, limited flexibility in the frequency and amplitude control of the output signal, and susceptibility of the system to interference from an electrosurgical unit. These problems are overcome by utilizing a digital ultrasonic generator system, which is controlled by switches on the generator console, foot activated pedals, and hand activated switches mounted on a hand activation assembly attached to the hand piece.

In an illustrative embodiment of the invention an ultrasonic generator and control system is housed in a console. Connected to the console by a cable is a hand piece that includes a piezoelectric transducer attached by a mechanical amplifying structure to a surgical blade or scalpel. The cable applies an electric current drive signal from the generator to the transducer to cause it to vibrate longitudinally. The structure and blade have a principle resonance frequency, so that when the proper electrical signal is applied to the transducer, the blade will vibrate back and forth with significant longitudinal displacement (e.g., 40 to 100 microns) and at an ultrasonic rate of speed. For a given load the greater the current, the larger the longitudinal displacement amplitude.

A switch assembly attached to the hand piece may allow the surgeon to activate and deactivate the generator to drive the ultrasonic blade on and off respectively. The switch is wired to the console via the hand piece cable. In addition, it is typical to provide a foot switch as a way of activating the ultrasonic blade in the same manner as explained for hand activation. Such a foot switch is connected to the generator by way of another cable which extends from the foot switch to the generator console. Further, other control switches and indicators are provided on the console.

According to the present invention, the core frequency control portion of a typical analog ultrasonic generator is replaced with a digital system that provides increased capabilities that assist in ameliorating some of the problems inherent in the prior art. The digital core includes a digital signal processor or microcontroller, which controls the frequency and sets the desired amplitude of the output ultrasonic signal as well as other system functions.

The generator uses a current amplitude feedback loop to set the drive current at a level selected by the user. Setting the desired power level is set by the user via switches on the console front panel, which level provides an indication to the processor of the output current level required. The processor produces a digital signal representative of the required current level, which is converted into an analog signal that controls the amplitude of a frequency signal also produced by the processor, that is supplied as an input to a push-pull amplifier. Before being supplied as an input to the amplifier, this signal is compared to a signal from a current sensor at the transducer to create an outer current control loop allowing the processor to change the drive current set point on the fly during operation. A change of the current set point is utilized only when the processor needs to adjust the output drive current set point during operation in the non-constant current portion of the power versus load curve, in order to create a specific power curve shape it is programmed to generate.

The constant output current control loop has a sensor which senses: the output drive current into the hand piece transducer. This sensed value is compared with the signal designating the output drive current set point (i.e. the required current) supplied by a direct digital synthesis (DDS) circuit. The difference is fed into the input of the push-pull amplifier. In turn, the amplifier delivers the appropriate output voltage to maintain the desired constant drive current.

A switching power supply in the form of an adjustable Buck regulator supplies D.C. voltage to the push-pull amplifier. The level of the output voltage supplied by the Buck regulator to the push-pull amplifier is determined by sensing the amplifier output minimum voltage which is required such that the amplifier will operate under the most efficient conditions without dissipating unnecessary or excess power and comparing it to a fixed reference.

In order to set the generator operation at the resonance of the hand-piece transducer, the microprocessor produces a frequency signal that sweeps either from above or below the target resonance frequency in search for this resonance. The current and voltage sensors at the transducer provide signals to the processor enabling it to calculate the instantaneous impedance of the transducer and blade combination. A change in this impedance along with a change in the current-to-voltage phase angle indicates resonance. The frequency signal from the processor is digital, but is converted to an analog signal by the direct digital synthesizer (DDS), whose output amplitude (i.e. full scale of its output) is controlled by the current set point signal. The voltage and current sensor signals are also provided to zero crossing detectors that control the starting and stopping of a counter driven by an oscillator with fixed and precise frequency. As a result, the digital value in the counter is an indication of the output current to output voltage phase angle or difference. This digital signal is provided to the processor which compares it to a digital phase angle set point, a process that generates an error input signal for the resonance frequency control loop. This error signal is applied to a phase error correction algorithm whose output is the digital representation of the frequency of the signal that drives the push-pull amplifier so as to complete the frequency close loop control. Thus, the system has a digitally controlled frequency as well as current set point amplitude loops. This provides significant flexibility and accuracy.

Using this digital topology in the generator makes it possible to achieve increased consistency of harmonic scalpel performance by better control of the electrical signals driving the transducers which resonate the ultrasonic blade. The described topology allows the system to individually regulate the three elements of output current, output voltage and output power. This provides flexibility such that the power versus load curve can be tailored for specific hand pieces and/or blade types to allow for the delivery of desired tissue effects.

The system also provides hardware based safety mechanism by which output current in excess of the maximum allowed current for each specific power level can not be delivered into the hand piece transducer, such that unsafe excess displacement of the ultrasonic blade tip is prevented. In addition to preventing unsafe excess displacement of the ultrasonic blade, this mechanism ensures both transducer and blade operate in a region that is best for their reliability. This is achieved by sensing the output current and comparing it, with a set of comparators, to individual set points for each of the designated power levels selectable by the user. The system output drive is shut down when the output current is determined to be in excess of the maximum allowed current level for the specific power level utilized. When not controlling the current for the designated power levels during normal operation, this arrangement is also utilized to ensure the current during diagnostic tests is not in excess of the designated output current for the user initiated diagnostic mode.

To allow the drive signals to be tailored for individual hand pieces and/or blades, the following key parameters affecting the system electrical output signals are stored in non-volatile memory embedded in the hand piece cable: (1) current set point (optimal current level to drive the particular transducer while in the constant current region of the output power versus load curve); (2) maximum output voltage (along with the current set point that designates the maximum output power drive); (3) regulation mode (identifies the parameter the generator is required to regulate, e.g. voltage or power, as the load increases beyond the point were the maximum output power of the generator has been reached); (4) maximum load point (the maximum load the generator should use to drive the specific hand piece utilized, larger loads should not be driven); and (5) frequency lock range (designates the frequency range for both the seek and maintain sweep range in search for resonance.

In addition, the digital system provides improved performance (at start up and under load, minimal performance degradation with temperature variations, and reduced tolerance requirements form the transducer and blade designs. It also provides consistency between hand pieces (current and voltage drive level requirements are set during the manufacturing process of the transducer) and extended useful life of the hand piece. These benefits are achieved by employing a topology that includes a digital signal processor (DSP), a direct digital synthesis (DDS) circuit, a digital phase detection scheme, and direct sensing of transducer current and applied voltage which are digitally fed into the DSP to achieve tight analog regulation of output current drive by having the microprocessor control and regulate the output drive frequency. The benefits are also achieved by utilization of the microprocessor software control to change the current set point for the analog closed loop output current regulation circuit during operation, which allows switching to voltage or power regulation as desired.

Another key advantage of the system is that it has a frequency lock range that is temperature stable, free of the effects of electronic component variability, and as narrow as required. The range is digitally set as parameter stored inside the hand piece in non volatile memory. It also has the ability to sweep the output frequency in either up or down directions, as well as to hop in frequency, such that the transition between one frequency and another occurs at the zero crossing of the sine wave, which ensures minimal distortion of the signal, thereby preventing erroneous operation and minimizing electromagnetic interference. This results in related relaxed design tolerances for the transducers and blades. The frequency can also be swept for diagnostic purposes where individual frequencies are set, output current drive levels are set, and measurements of transducer behaviors are monitored by sensing the output drive voltage and current-to-voltage phase angle, which allows an impedance calculation. Furthermore, the output drive signal can be controlled such that the output current, voltage and power can be regulated.

In order to avoid accidental contact with tissue during a user initiated diagnostic tests, the tests can be initiated by two switch operations. For example, the diagnostic test may be initiated by activation of a button on the front panel of the generator and the foot pedal switch or the hand piece switch. This requirement for a combination of switches to activate the diagnostic mode helps to eliminate the possibility of accidental movement of the blade while it is either in contact with tissue or another object, which could result in incorrect diagnostic results or harm to the user.

The inventive ultrasonic generator can further be arranged so that it can be automatically disabled in the presence of electrical interference from an Electro-surgical Unit. This is accomplished by equipping the generator with a noise emission detector. When noise of this type is detected, the activation of the ultrasonic surgical system is inhibited. This noise emission detector may be in the form of an antenna created by the hand piece cable or by pick-up coils located inside the hand piece or console of the generator.

BRIEF DESCRIPTION OF THE DRAWINGS

The foregoing and other features of the present invention will be more readily apparent from the following detailed description and drawings of an illustrative embodiment of the invention in which:

FIG. 2 is a schematic view of a cross section through the ultrasonic scalpel hand piece;

FIG. 5 is a graph of phase slope vs. Impedance at 0° Phase for the system of FIG. 3.

DESCRIPTION OF ILLUSTRATIVE EXEMPLARY EMBODIMENTS

Figure 1:
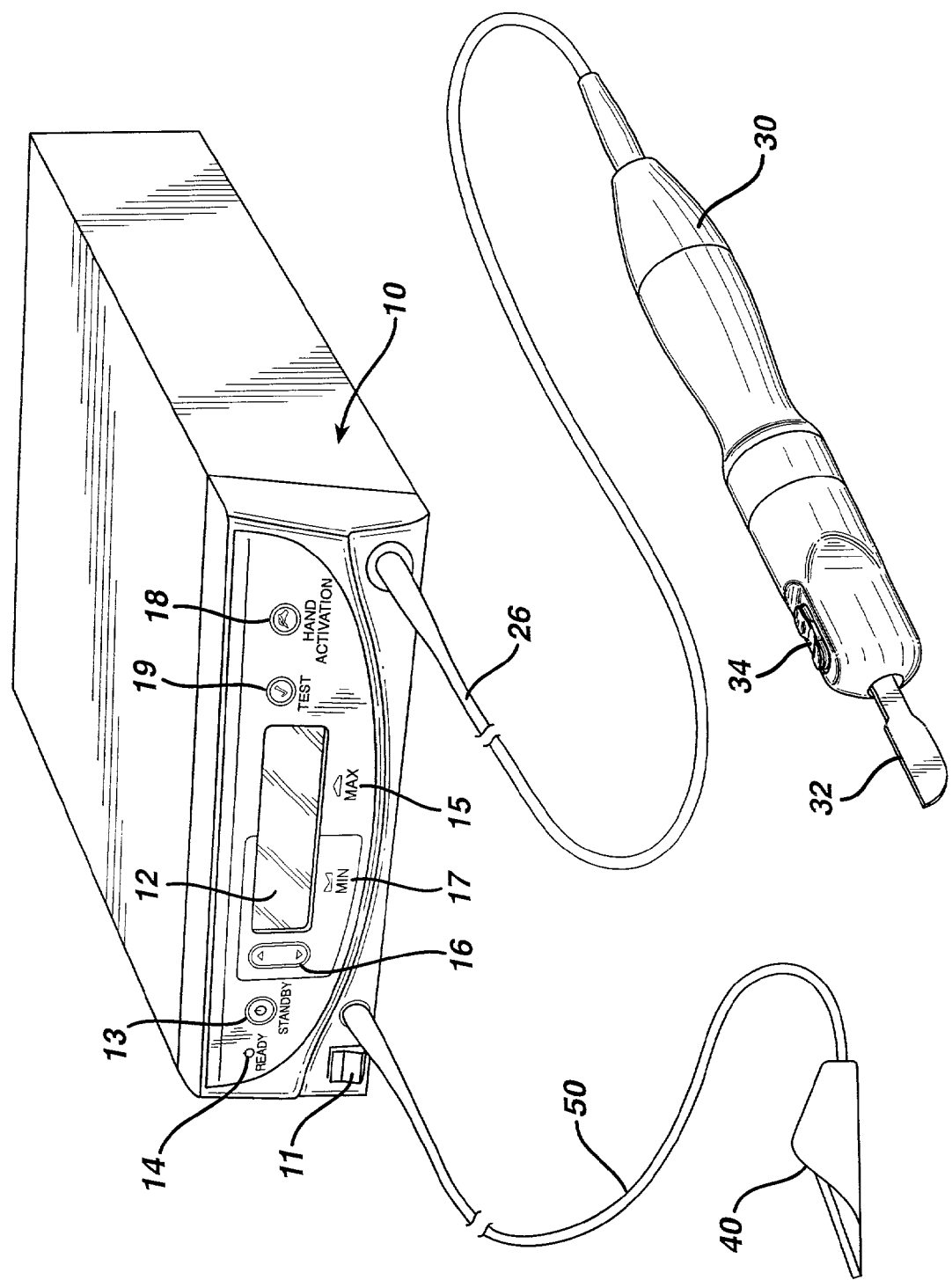
FIG. 1 is an illustration of a console for an ultrasonic surgical cutting and hemostasis system, as well as a hand piece and foot switch, in accordance with an exemplary embodiment of the present invention.

FIG. 1 shows an illustration of a console or housing 10 for an ultrasonic generator and a control system for the ultrasonic surgical system of the present invention. By means of a first set of wires in cable 20, electrical energy, i.e., drive current, is sent from the console 10 to a hand piece 30 where it imparts ultrasonic longitudinal movement to a surgical device, such as a sharp scalpel blade 32. This blade can be used for simultaneous dissection and cauterization of tissue. The supply of ultrasonic current to the hand piece 30 may be under the control of a switch 34 located on the hand piece, which is connected to the generator in console 10 via a wire in cable 20. The generator may also be controlled by a foot switch 40, which is connected to the console 10 by another cable 50. Thus, in use a surgeon may apply an ultrasonic electrical signal to the hand piece, causing the blade to vibrate longitudinally at an ultrasonic frequency, by operating the switch 34 on the hand piece with his finger, or by operating the foot switch 40 with his foot.

The generator console 10 includes a liquid crystal display device 12, which can be used for indicating the selected cutting power level in various means such, as percentage of maximum cutting power or numerical power levels associated with cutting power. The liquid crystal display device 12 can also be utilized to display other parameters of the system. Power switch 11 is used to turn on the unit. While it is warming up, the "standby" light 13 is illuminated. When it is ready for operation, the "ready" indicator 14 is illuminated and the standby light goes out. If the unit is to supply maximum power, the MAX button 15 is depressed. If a lesser power is desired, the MIN button 17 is activated. This automatically deactivates the MAX button. The level of power when MIN is active is set by button 16.

If a diagnostic test is to be performed, it is initiated by the "test" button 19. For safety reasons, e.g., to make sure a test is not started while the blade is touching the surgeon or other personnel, the button 19 must be pressed in combination with hand piece switch 34 or foot switch 40. Also, if the hand switch 34 is to be operative instead of foot switch 34, "hand activation" button 18 on the front panel must be operated.

When power is applied to the ultrasonic hand piece by operation of either switch 34 or 40, the assembly will cause the surgical scalpel or blade to vibrate longitudinally at approximately 55.5 kHz, and the amount of longitudinal movement will vary proportionately with the amount of driving power (current) applied, as adjustably selected by the user. When relatively high cutting power is applied, the blade is designed to move longitudinally in the range of about 40 to 100 microns at the ultrasonic vibrational rate. Such ultrasonic vibration of the blade will generate heat as the blade contacts tissue, i.e., the acceleration of the blade through the tissue converts the mechanical energy of the moving blade to thermal energy in a very narrow and localized area. This localized heat creates a narrow zone of coagulation, which will reduce or eliminate bleeding in small vessels, such as those less than one millimeter in diameter. The cutting efficiency of the blade, as well as the degree of hemostasis, will vary with the level of driving power applied, the cutting rate of the surgeon, the nature of the tissue type and the vascularity of the tissue.

As illustrated in more detail in FIG. 2, the ultrasonic hand piece 30 houses a piezoelectric transducer 36 for converting electrical energy to mechanical energy that results in longitudinal vibrational motion of the ends of the transducer. The transducer 36 is in the form of a stack of ceramic piezoelectric elements with a motion null point located at some point along the stack. The transducer stack is mounted between two cylinders 31 and 33. In addition a cylinder 35 is attached to cylinder 33, which is mounted to the housing at another motion null point 37. A horn 38 is also attached to the null point on one side and to a coupler 39 on the other side. Blade 32 is fixed to the coupler 39. As a result, the blade 32 will vibrate in the longitudinal direction at an ultrasonic frequency rate with the transducer 36. The ends of the transducer achieve maximum motion with a portion of the stack constituting a motionless node, when the transducer is driven with a current of about 380 mA RMS at the transducers' resonant frequency. However, the current providing the maximum motion will vary with each hand piece and is a valve stored in the non-volatile memory of the hand piece so the system can use it.

The parts of the hand piece are designed such that the combination will oscillate at the same resonant frequency. In particular, the elements are tuned such that the resulting length of each such element is one-half wavelength. Longitudinal back and forth motion is amplified as the diameter closer to the blade 32 of the acoustical mounting horn 38 decreases. Thus, the horn 38 as well as the blade/coupler are shaped and dimensioned so as to amplify blade motion and provide harmonic vibration in resonance with the rest of the acoustic system, which produces the maximum back and forth motion of the end of the acoustical mounting horn 38 close to the blade 32. A motion at the transducer stack is amplified by the horn 38 into a movement of about 20 to 25 microns. A motion at the coupler 39 is amplified by the blade 32 into a blade movement of about 40 to 100 microns.

Figure 3A:
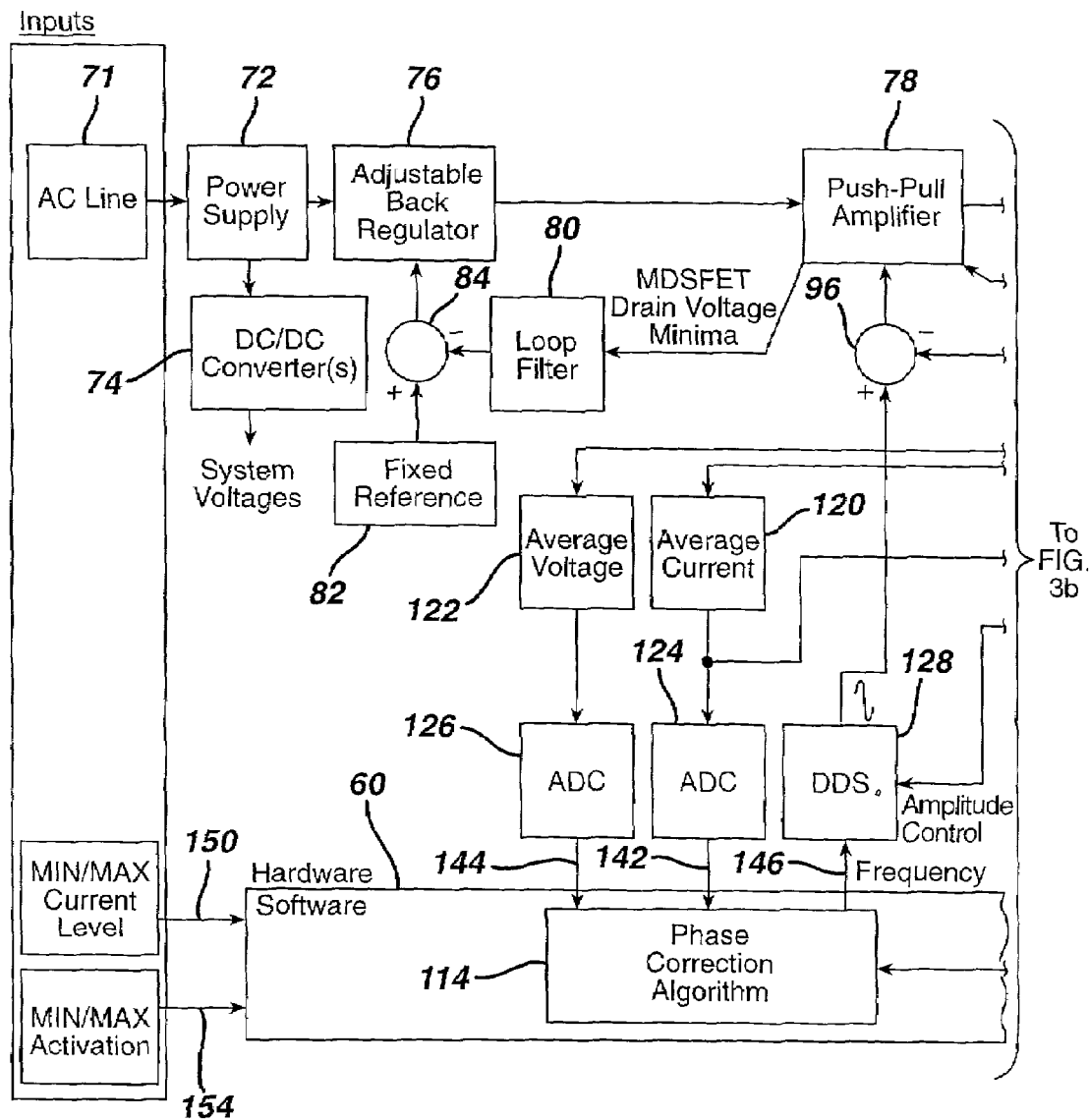
FIGS. 3a and 3b is a block diagram illustrating the ultrasonic system according to an embodiment of the present invention.

The system which creates the ultrasonic electrical signal for driving the transducer in the hand piece is illustrated in FIG. 3. This drive system is flexible and can create a drive signal at a desired frequency and power level setting. A microprocessor 60 in the system is used for monitoring the appropriate power parameters and vibratory frequency as well as causing the appropriate power level to be provided in either the cutting or coagulation operating modes.

A.C. power from a line 71 is provided to the power supply 72. This power may be from 90 to 267 volts RMS at 50 to 60 cycles. The power supply sends part of the input, i.e., a 48 vac signal to a D.C. to D.C. converter 74 which uses this regulated A.C. voltage to create the low D.C. system voltages needed to operate the electronic circuits for the rest of the system, e.g., ±15 volts DC and ±5 volts DC.

The power supply 72 also provides a 48 vac signal to Adjustable Buck regulator 76, which is a switching regulator that changes the 48 vac to a lower D.C. signal that is required as a supply voltage by a push-pull amplifier 78. The output of amplifier 78 is applied to a transformer 86 (FIG. 3b), which provides an isolated signal over line 85 to the piezoelectric transducer 36 in hand piece 30. This transducer drives the scalpel blade 32. The transformer 86 has about a 1:7 voltage step up ratio and its main purpose is to isolate the patient circuit represented by the hand piece transducer 36 of the hand piece from the amplifier 78.

A signal is tapped off the drains of one of the field effect transistors in the push-pull amplifier 78. This signal, which is indicative of the output voltage, is passed through a loop filter 80 and is applied to the minus input of a summing node 84. The plus input to node 84 has a fixed reference voltage 82 applied to it. The output of node 84 is fed to the Buck regulator 76. This output generates a feed back control loop from the push-pull amplifier 78 to the Buck regulator 76, through loop filter 80, and summing node 84. The push-pull amplifier can operate over a range of approximately of 5 to 44 volts D.C. supply voltage from the Buck regulator. However, if the amplitude of the output voltage for a particular power setting is low and the Buck regulator output voltage is high, the push pull amplifier 78 must produce a voltage drop to compensate. This makes operation of the amplifier inefficient. However, in this case the output voltage of the Buck regulator 76 is lowered via the feedback mechanism arrangement of the line tapped off the drains of the two field effect transistors that make up the main circuit of the push-pull amplifier 78, the loop filter 80, the summing node 84, and the fixed reference 82. The signal applied to the loop filter 80 is near ground level if the transistors are dissipating a normal amount of power. If the transistors are dissipating more power, the drain voltage is higher, and that voltage drives the Buck regulator 76 through loop filter 80 and the summing node 84 to lower its supply voltage to the push-pull amplifier 78. As a switching regulator, the Buck circuit 76 can create a voltage drop in an efficient manner, as opposed to the push-pull amplifier 78 which is a linear amplifier.

The loop filter 80 keeps the push-pull amplifier 78 and supply voltage feedback loop from becoming unstable. The fixed reference 72 makes sure that the supply voltage to the push-pull amplifier 78 is at least a certain amount above the minimum supply voltage required by the push-pull amplifier 78 in order to operate linearly, such that it does not generate a distorted output voltage sine wave. This guarantees efficient operation of the push-pull amplifier 78 as the supply voltage to it from the Buck regulator 76 is raised or lowered as more or less output voltage is required to deliver the required current level.

A current sense 88 (FIG. 3b), in the form of a second isolation transformer across a sense resistor, senses the amount of current in line 85 at the input to the transducer 36. In addition, voltage sense 92, in the form of a third isolation transformer, measures the voltage at the input line 85 to the transducer 36. The current sense signal is applied to stabilizing loop filter 94, whose output is compared to a variable set point in a summing node 96. The creation of the set point will be described below. The output of node 96 drives the push-pull amplifier 78 at a current amplitude maintained by the feedback loop of current sense 88, loop filter 94 and node 96. This is a current amplitude control loop.

Figure 3B:
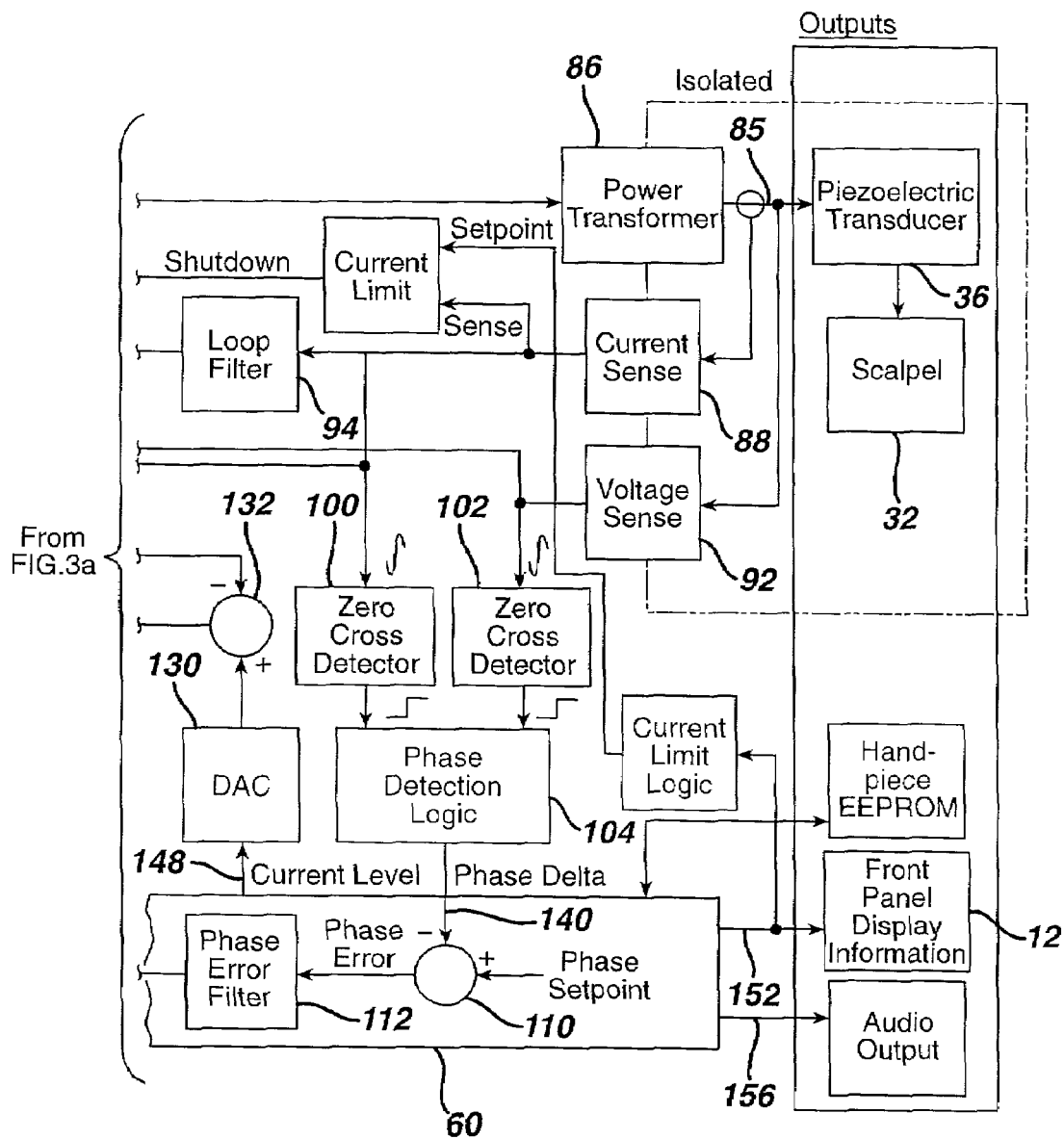

The signal from current sense 88 and the voltage sense 92 are applied to zero crossing detectors 100 and 102, respectively (FIG. 3b). These detectors produce output pulses whenever the current and voltage signals cross zero. The current zero crossing signal is applied to the start input of a counter (not shown) in phase detection logic 104, while the voltage zero cross signal is applied to the stop input of the counter in the phase detection logic 104. An oscillator (not shown) providing a clock signal operating, e.g., at 40 MHz, is located in the detection logic 104. It drives the counter from the start pulse to the stop pulse. As a result, the count of the counter is related to the current/voltage phase difference or delta in the signal applied to the transducer. The larger the count, the greater the phase delta. The phase detection logic may also perform other functions and may be implemented with a programmable logic array. With the 40 MHz clock and a 55.5 KHz nominal transducer drive frequency, the phase detection logic 108 provides a phase resolution of approximately 0.5°.

Figure 4:
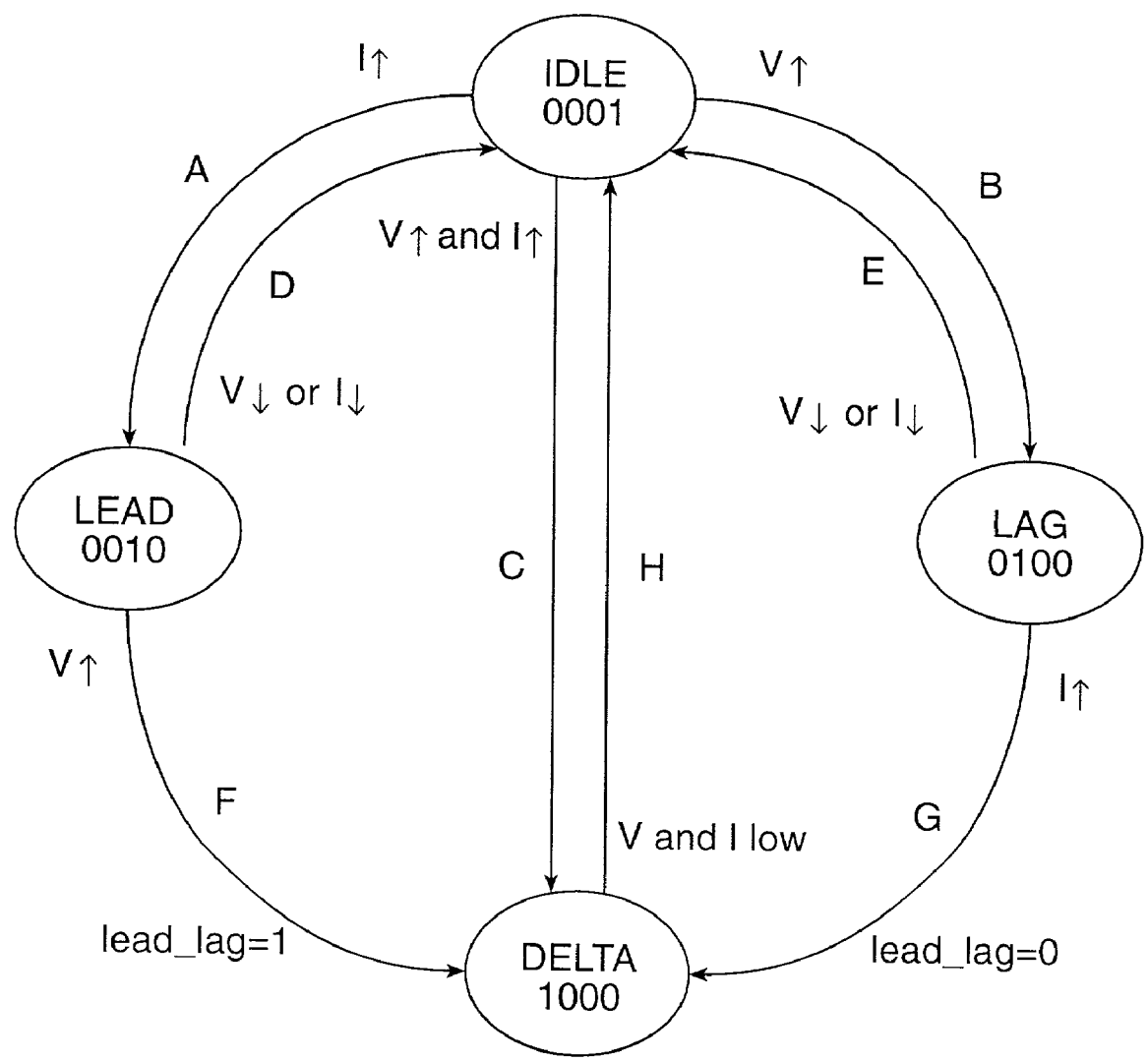
FIG. 4 is a state diagram for a portion of the operation of the phase detection logic of the system shown in FIG. 3.

The phase detection logic further executes routines equivalent to two phase delta state machines, one for a raising edge phase delta and one for a falling edge delta. Each of these is made available to the DSP through a register interface. The state machine operation for a rising edge zero crossing detection is shown in FIG. 4 and begins in the IDLE state (0001). A rising current edge sends it to the LEAD state (0010), A in FIG. 4, while a rising voltage edge sends it to the LAG state (0100), B in FIG. 4. This causes the phase counter to increment or decrement, respectively, a the 40 MHz rate. It is also possible for concurrent voltage and current rising edges to occur, e.g., when at zero phase. In this case, the state machine goes directly to DELTA state (1000), i.e., C in FIG. 4. The counter value is captured, but it should be zero.

Once in the LEAD or LAG state, if any falling edge is seen before the rising edge of the other signal, the state machine resets to the IDLE state (0001), i.e., D or E, respectively. Since the transducer phase range is only >>±90°, these two situations represent an abnormal case and will preclude a phase measurement until the next legitimate sequence is seen. The early falling edge is assumed to have been caused by multiple zero crossings of a noisy signal. As a result, the phase counter is disabled and reset to zero.

When in the LEAD state (0010), a rising voltage signal sends the machine to the DELTA state (1000), i.e., F, which indicates that a legitimate current leading positive phase) cycle has been detected. In the LAG state (0100), a rising current signal sends the machine to the DELTA state, i.e., G. Again, a legitimate cycle has been detected. But in this case it is a current lagging (negative phase) cycle.

In the DELTA state, the phase counter is stopped, the counter value, which represents the phase reading, is captured, the value is copied to a register in order to make the reading available to the DSP, and the counter is reset. Further, when in DELTA state, if both signals are low, the machine returns to the IDLE state, path H. As a result, the phase counter is reset to zero.

The diagram of FIG. 4 is of the rising edge zero cross detection state machine. The falling edge state machine can be easily derived by inverting the logic of the voltage and current signals.

The phase delta, which is a digital count, is provided to the digital signal processor (DSP) or microprocessor 60 over line 140. It is used as the negative input to a summing node 110 in the DSP or microprocessor, while a stored digital phase set point number is applied to the positive input. The output of node 110 is a digital phase error. The digital phase error signal is passed through a phase error filter 112, which acts to stabilize the circuit. In turn the filtered phase error signal is used by a phase correction algorithm implemented 114 also by the DSP or microprocessor 60. A change of the current set point is utilized only when the processor needs to adjust the output drive current set point during operation in the non-constant current portion of the power versus load curve, in order to create a specific power curve shape it is programmed to generate.

Signals from the current sense 88 and voltage sense 92 are also applied to current and voltage averaging circuits 120 and 122, respectively, which are in the form of full wave rectifier and averaging circuits. The measured signals are converted to RMS current and voltage values through known scaling factors. This conversion to RMS values provides the most accuracy only when the monitored waveform is sinusoidal. The more non-sinusoidal distortion in the signal, the less accurate the reading. Since the current and voltage waveforms are usually close to sinusoidal, the measurement technique is appropriate. Harmonic distortion, which is also sinusoidal, superimposed on the fundamental drive signal does not negatively affect this measurement.

The drive voltage of the harmonic scalpel transducer exhibits asymmetrical harmonic distortion. Because it is asymmetrical, it must be composed of even and odd harmonics. The distortion is most evident when the voltage, and therefore the mechanical load on the blade, are low. This is because the magnitude of the harmonics is unaffected by the mechanical loading. Thus, at low mechanical load the harmonic contribution is a much higher percentage of the signal. It is not reasonable to reduce this distortion since the distortion is a mechanical effect caused by feedback from the excitation of secondary resonance(s). The distortion can have a negative effect on the ability to measure the impedance phase and magnitude.

Implementation of a filter with discrete components or the DSP could give a more accurate measurement of the primary resonance impedance. The result would be more sinusoidal, but not an accurate measurement of the total impedance, since the harmonics do contribute. However, the full-wave rectified averaging method chosen to measure impedance magnitude is relatively immune to the affects of the harmonic distortion. The challenge is to minimize the impact on the measurement of the impedance phase. The method chosen to measure phase is to measure the distance between the zero crosses of the voltage and current signals. When the harmonic distortion appears near the zero crossing of a signal, it can cause the location of the zero crossing to vary significantly. Also, the harmonic distortion usually causes the voltage waveform to have other than a 50% duty cycle. Measuring the "phase" at the rising edge zero crosses yields an entirely different reading than the "phase" at the falling edge zero crosses. Averaging the two readings provides a more accurate phase reading, but would still have significant error if the harmonic distortion was not centered about the crest of the voltage waveform. Using the average of the falling edge and the rising edge phase measurements as the accepted phase reading, and regulating to a target of 0° phase, causes the harmonic distortion to center about the crest of the voltage waveform. The affects of the harmonic distortion are, therefore, minimized to an acceptable degree with this architecture and processing.

In implementing this concept, the analog average value signals created by circuits 120, 122 are converted by respective analog-to-digital converters (ADC) circuits 124 and 126, respectively. By applying the digital outputs of ADC 124, 126, which represent the average current and voltage applied to the transducer 36, to the DSP or microprocessor over input lines 142, 144 can calculate the instantaneous average impedance of the transducer to be utilized for the phase correction algorithm 114.

Since the DSP 60 or microprocessor, when implementing the phase correction algorithm 114 calculates and knows the impedance and the phase error of the signals driving the transducer, it can generate the frequency signal 146 for the system so that it locates the resonance frequency for the transducer/blade assembly. For example, under the control of a program stored in the DSP or microprocessor 60 as the phase correction algorithm, the frequency during startup can be made to be a set value, e.g., 50 kHz. It can than be caused to sweep up at a particular rate until a change in impedance, indicating the approach to resonance, is detected. Then the sweep rate can be reduced so that the system does not overshoot the resonance frequency, e.g., 55 kHz. The sweep rate can be achieved by having the frequency change in increments, e.g., 50 cycles. If a slower rate is desired, the algorithm program can decrease the increment, e.g., to 25 cycles which both can be based adaptively on the measured transducer impedance magnitude and phase. Of course, a faster rate can be achieved by increasing the size of the increment. Further, the rate of sweep can be changed by changing the rate at which the frequency increment is updated.

If it is known that there is an undesired resonant mode, e.g., at say 51 kHz, the program can cause the frequency to sweep down, e.g., from 60 kHz, to find resonance. Also, the system can sweep up from 50 kHz and hop over 51 kHz where the undesired resonance is located. In any event, the system has a great degree of flexibility.

To carry out this operation it is necessary to implement a transducer drive phase control algorithm that seeks and then maintains the desired phase angle between the transducer voltage and the transducer current. The transducer drive phase is dependent on the frequency of the drive signal. However, the desired phase will not always be found at the same frequency because it is dependent on the characteristics of the transducer. These characteristics can vary from transducer to transducer, and over temperature.

The parameters controlling the drive control algorithm are the transducer impedance average magnitude, and the transducer impedance average phase. The outputs of this algorithm are the frequency set point to a DDS (Direct Digital Synthesis) and the transducer current magnitude set point. Utilizing the algorithm, the DSP first seeks the target 0° impedance phase delta. The frequency of the DDS is set to an off-resonance frequency that is lower than the resonance of any known transducer/blade combination. When off resonance, the impedance magnitude of the system is very high. In order for the voltage to not exceed the physical limit of the system, the current is set very low. The frequency is then smoothly increased until the target 0° impedance phase delta is found. As resonance approaches, a corresponding drop in the impedance magnitude occurs. The current set point can be raised to the point that the voltage magnitude falls just below the physical limit of the system. The frequency must be smoothly ramped to avoid oscillation of the transducer impedance magnitude and phase. Oscillation occurs when the seeking results in a rate of change of displacement (dd/dt) which exceeds the maximum dd/dt which occurs in the natural mechanical resonance of the blade and hand piece. The frequency step to be used is dependent on the transducer impedance magnitude and phase. A two dimensional lookup table, of which the impedance phase and magnitude are the two indices, can be used to contain the frequency step values. The higher the impedance magnitude and phase, the higher the frequency step. The frequency step is applied at a rate of 2 KHz or greater.

Once the target phase delta has been found, it must be maintained. The frequency at which the target 0° impedance phase occurs can drift due to temperature change of the transducer, or it can move rapidly due to a mechanical load change at the hand piece. To maintain the target 0° impedance phase, the impedance phase and magnitude are measured and used to determine a frequency correction (see FIG. 5, Phase Slope vs. Impedance at 0° Phase):

$$f_D = f * \text{phase\_slope}(|z|) * k$$

where $f_D$=the calculated frequency change, f=phase reading, z=impedance, k=a scaling factor. The frequency/phase slope vs. impedance magnitude curve was determined through a mathematical modeling of the transducer. It should be noted that the phase slope curve does not change significantly for these purposes for approximately ±40° from 0° phase. Therefore the curve will still be applicable even when slightly off resonance. The scaling factor is a fractional number less than 1 which is applied to prevent overshoot. This is necessary due to a delay in impedance phase and magnitude measurements due to filtering. The impedance magnitude and phase readings are filtered with a moving window average routine. This correction function is applied at a 1 KHz rate.

As shown in FIG. 3, the digital frequency signal 146 from the phase correction algorithm 114 is applied to direct digital synthesis (DDS) circuit 128. DDS 128 is a numerically controlled oscillator whose analog sine wave output frequency varies according to a digital frequency code input, such as signal 146.

In operation, the user sets a particular power level to be used with the surgical instrument. This is done with power level selection switch 16 on the front panel of the console. The switch generates signals 150 that are applied to the DSP 60. The DSP 60 then displays the selected power level by sending a signal on line 152 (FIG. 3b) to the console front panel display 12. Further, the DSP 60 generates a digital current level signal 148 that is converted to an analog signal by digital-to-analog converter (DAC) 130. The resulting reference analog signal is applied as a current set point to summing node 132. A signal representing the average output current from circuit 120 is applied to the negative input of node 132. The output of node 132 is a current error signal or amplitude control signal which is applied to DDS 128 to adjust the amplitude of its output, as opposed to the frequency of its output, which is controlled by the signal on line 146 from the DSP 60. The arrangement of current level signal 148, DAC 130, summing node 130, and signal supplied by average output voltage 122 allows the DSP to adjust the output current such that it can generate a desired power versus load curve when not in constant current mode.

The digital frequency signal 146 and analog amplitude control signal from node 132 are converted by the DDS 128 to an analog output signal that is applied to summing node 96 as the positive input. The negative input to node 96 is the output of current sense 88 after it has been passed through a loop-stabilizing filter 94. The output of node 96 is the drive signal for the push-pull amplifier 78, whose supply voltage is under the control of the loop with the adjustable Buck regulator 76.

To actually cause the surgical blade to vibrate, the user activates the foot switch 40 or the hand piece switch 34. This activation puts a signal on line 154 in FIG. 3a. This signal is effective to cause power to be delivered from push-pull amplifier 78 to the transducer 36. When the DSP 60 has achieved phase lock at the hand piece transducer resonance frequency and power has been successfully applied to the hand piece transducer, an audio drive signal is put on line 156. This causes an audio indication in the system to sound, which communicates to the user that power is being delivered to the hand piece and that the scalpel is active and operational.

Using digital control of the generator makes it possible to achieve increased consistency of harmonic scalpel performance by better control of the electrical signals driving the transducers 36 which resonate the ultrasonic blade 32. This digital system can individually regulate the three elements of output current, output voltage and output power. This provides flexibility such that the power versus load curve can be tailored for specific hand pieces and/or blade types to allow for the delivery of desired tissue effects.

The system also provides hardware based safety mechanism by which output current in excess of the maximum allowed current for each specific power level can not be delivered into the hand piece transducer, such that unsafe excess displacement of the ultrasonic blade tip is prevented. This is achieved by storing a maximum current value in the system and having DSP 60 compare the average current from circuit 120 to that value. If it is exceeded, the system can automatically shut down.

In addition to preventing unsafe excess displacement of the ultrasonic blade, the digital control can be use to ensures both transducer and blade operate in a region that is best for their reliability. This is achieved by sensing the output current and comparing it, with a set of comparators, to individual set points for each of the designated power levels selectable by the user. The system output drive is shut down when the output current is determined to be in excess of the maximum allowed current level for the specific power level utilized.

When not controlling the current for the designated power levels during normal operation, the digital system can be use to ensure that the current during diagnostic tests is not in excess of the designated output current for the user initiated diagnostic mode.

To allow the drive signals to be tailored for individual hand pieces and/or blades, the following key parameters affecting the system electrical output signals can be stored in non-volatile memory embedded in the hand piece cable: (1) current set point (optimal current level to drive the particular transducer while in the constant current region of the output power versus load curve); (2) maximum output voltage (along with the current set point that designates the maximum output power drive); (3) regulation mode (identifies the parameter the generator is required to regulate, e.g. voltage or power, as the load increases beyond the point were the maximum output power of the generator has been reached); (4) maximum load point (the maximum load the generator should use to drive the specific hand piece utilized, larger loads should not be driven); and (5) frequency lock range (designates the frequency range for both the seek and maintain sweep range in search for resonance. The DSP can then read these values and control the generation of the ultrasonic frequencies to assure that the hand piece is operated efficiently and safely.

In addition, the digital system provides improved performance (at start up and under load, minimal performance degradation with temperature variations, and reduced tolerance requirements form the transducer and blade designs. It also provides consistency between hand pieces (current and voltage drive level requirements are set during the manufacturing process of the transducer) and extended useful life of the hand piece. These benefits are achieved by employing the DSP, the direct digital synthesis (DDS) circuit, the digital phase detection scheme, and direct sensing of transducer current and applied voltage which are digitally fed into the DSP to achieve tight regulation of the output current drive by having the DSP control and regulate the output drive frequency. The benefits are also achieved by utilization of the microprocessor software control to change the current set point for the analog closed loop output current regulation circuit during operation, which allows switching to voltage or power regulation as desired.

Another key advantage of the system is that the digital system provides a frequency lock range that is temperature stable, free of the effects of electronic component variability, and as narrow as required. The range can be digitally set as parameter stored inside the hand piece in non volatile memory. The system also has the ability to sweep the output frequency in either up or down directions, as well as to hop in frequency, such that the transition between one frequency and another occurs at the zero crossing of the sine wave, which ensures minimal distortion of the signal, thereby preventing erroneous operation and minimizing electromagnetic interference. This results in related relaxed design tolerances for the transducers and blades. The frequency can also be swept for diagnostic purposes where individual frequencies are set, output current drive levels are set, and measurements of transducer behaviors are monitored by sensing the output drive voltage and current-to-voltage phase angle, which allows an impedance calculation. Furthermore, the output drive signal can be controlled such that the output current, voltage and power can be regulated.

In order to avoid accidental contact with tissue during a user initiated diagnostic tests, the tests can be initiated by two switch operations. For example, the diagnostic test may be initiated by activation of a button on the front panel of the generator and the foot pedal switch or the hand piece switch. This requirement for a combination of switches to activate the diagnostic mode helps to eliminate the possibility of accidental movement of the blade while it is either in contact with tissue or another object, which could result in incorrect diagnostic results or harm to the user.

The inventive ultrasonic generator can further be arranged so that it can be automatically disabled in the presence of electrical interference from an Electro-surgical Unit. This is accomplished by equipping the generator with a noise emission detector. When noise of this type is detected, the activation of the ultrasonic surgical system is inhibited. This noise emission detector may be in the form of an antenna created by the hand piece cable or by pick-up coils located inside the hand piece or console of the generator.

While the invention has been particularly shown and described with reference to preferred embodiments thereof, it will be understood by those skilled in the art that various changes in form and details may be made therein without departing from the spirit and scope of the invention.

We claim:

1. An ultrasonic surgical system including a controllable ultrasonic energy generator, a hand piece with a blade that is vibrated at an ultrasonic resonance frequency rate by energy from the generator, and a switch for indicating to the generator the amplitude and frequency of the energy supplied to the hand piece, said ultrasonic generator comprising:
   an analog input drive signal generator which generates an input drive signal having an amplitude and frequency;
   an amplifier which receives the analog input drive signal and supplies the energy through a transformer and the transformer output is fed to the hand piece through a line in response thereto;
   a current sensor that senses the current at the transformer output and produces a current signal related thereto;
   a comparator which compares the current signal to a variable preset current value and produces a difference signal that is applied to the analog input drive signal generator so as to change the amplitude of the drive signal to cause the current signal to match the preset value;
   a voltage sensor which senses the voltage at the transformer output and produces a voltage signal related thereto;
   microprocessor means for producing one or more frequency signals that sweeps either from above or below a target resonance frequency of the handpiece;
   a digital phase detector which compares the current signal to the voltage signal at the one or more frequency signals and generates a digital phase code related to the phase difference between them;
   a digital impedance detector which compares the ratio of the voltage signal to the current signal at the one or more frequency signals and generates a digital impedance code related thereto;
   a digital controller which receives the digital phase code and the digital impedance code and produces a digital frequency code in response thereto for determining the target resonance frequency of the hand piece; and
   a direct digital synthesis circuit for converting the digital frequency code to an analog frequency signal that is applied to the analog input drive signal generator so as to maintain the frequency at the resonance frequency.

2. The ultrasonic surgical system of claim 1 further including a controlled power supply for said amplifier which supplies power at a level to assure efficient operation of said amplifier.

3. The ultrasonic surgical system of claim 2 wherein the controlled power supply comprises:
   a fixed reference voltage;
   a comparator which compares the output of the amplifier to the fixed reference voltage and generates a power control signal in response thereto;
   an adjustable Buck regulator receiving a supply of power at one level and producing a supply of power at a different level based on the power control signal, the power at the different level being supplied to the amplifier.

4. The ultrasonic surgical system of claim 3 wherein the output of the amplifier is connected to said comparator by a loop filter.

5. The ultrasonic surgical system of claim 1 wherein the digital phase detector comprises:
   a voltage signal zero crossing detector which produces a voltage zero signal when said voltage signal crosses a zero axis;
   a current signal zero crossing detector which produces a current zero signal when said current signal crosses a zero axis;
   a circuit for measuring the time between the voltage zero signal and the current zero signal and producing a digital code related thereto.

6. The ultrasonic surgical system of claim 1 wherein the digital impedance detector comprises:
   a voltage averaging circuit which produces a voltage average signal based on the said voltage signal;
   a current averaging circuit which produces a current averaging signal based on said current signal; and
   wherein said digital controller continuously generates the ratio of the voltage average signal to the current average signal as an impedance signal, and wherein a change in said impedance signal as the drive signal frequency changes indicates an approach to said resonance frequency.

7. The ultrasonic surgical system of claim 1 further including a power level switch circuit which determines the preset current level.

8. The ultrasonic surgical system of claim 7 wherein the power level switch circuit comprises:
   a power level switch connected to said digital controller and causing said digital controller to produce a digital current level signal;
   a digital-to-analog convertor for changing the digital current level signal into an analog current level signal;
   a current averaging circuit which produces a current average signal based on the said current signal from said current sensor;
   a current comparator which compares the analog current level signal and the average current signal and produces an amplitude control signal, said amplitude control signal which is applied to the direct digital synthesis circuit to vary the amplitude of the analog frequency signal.

9. The ultrasonic surgical system of claim 8, wherein said analog input drive signal generator comprises a comparator which compares the analog frequency signal from the direct digital synthesis circuit and the current signal from the current sensor to produce the input drive signal of the amplifier.

10. The ultrasonic surgical system of claim 1, wherein during start up of the system causes the amplifier to generate an ultrasonic signal at a frequency near resonance, and to increment the frequency toward resonance while monitoring the outputs of said digital phase detector and digital impedance detector, and to halt the incrementing when these outputs indicate resonance of the hand piece.

11. The ultrasonic surgical system of claim 1 further including a memory which stores a maximum current to be delivered to a hand piece, and wherein the digital controller compares an average current signal to the maximum and halts the supply of energy to the hand piece when the average current exceeds the maximum.

12. The ultrasonic surgical system of claim 1 where in the digital controller includes a program which causes the amplifier to supply different current and voltage levels to the hand piece at different frequencies and to measure the current, voltage and phase to diagnose and test the operation of the system.

13. The ultrasonic surgical system of claim 12 further including a console for housing the generator, said console having a front panel, and wherein the diagnoses and testing is implemented in response to the activation of a button on the front panel and one of a foot pedal switch and a hand piece switch.

14. The ultrasonic surgical system of claim 1 further including a electrical interference detector which produces an output in response to the operation of an Electro-surgical Unit in the vicinity, and wherein the digital controller halts operation of the system in response to an output from said interference detector.

* * * * *